United States Patent [19]

Abou-Gharbia et al.

[11] Patent Number: 5,254,552
[45] Date of Patent: Oct. 19, 1993

[54] ARYL-AND HETEROARYL PIPERAZINYL CARBOXAMIDES HAVING CENTRAL NERVOUS SYSTEM ACTIVITY

[75] Inventors: Magid A. Abou-Gharbia, Glen Mills; John P. Yardley, Gulph Mills; Wayne E. Childers, Jr., Yardley, all of Pa.

[73] Assignee: American Home Products Corporation, New York, N.Y.

[21] Appl. No.: 852,119

[22] Filed: Mar. 16, 1992

Related U.S. Application Data

[60] Continuation of Ser. No. 533,974, Jun. 6, 1990, abandoned, which is a division of Ser. No. 493,179, Mar. 14, 1990, Pat. No. 5,010,078, which is a continuation-in-part of Ser. No. 335,075, Apr. 7, 1989, abandoned, which is a continuation-in-part of Ser. No. 297,460, Jan. 13, 1989, abandoned, which is a continuation-in-part of Ser. No. 197,890, May 24, 1988, abandoned.

[51] Int. Cl.$^5$ .............. A61K 31/495; C07D 295/145; C07D 401/04; C07D 401/14
[52] U.S. Cl. ................... 514/252; 514/253; 514/255; 544/360; 544/364; 544/373; 544/380
[58] Field of Search ............... 544/360, 373, 380, 364; 514/252, 253, 255

[56] References Cited

U.S. PATENT DOCUMENTS

| | | | |
|---|---|---|---|
| 3,624,086 | 11/1971 | Krimmel | 544/380 |
| 3,646,047 | 2/1972 | Wright | 546/202 |
| 3,734,915 | 5/1973 | Wright | 544/376 |
| 4,001,223 | 12/1975 | Sugimoto | 544/380 |
| 4,148,895 | 4/1979 | Lattrell et al. | 544/373 |
| 4,202,898 | 5/1980 | DePoortere | 514/255 |
| 4,748,247 | 3/1988 | Abou-Gharbia | 544/357 |
| 4,797,489 | 1/1989 | Abou-Gharbia | 544/331 |
| 4,882,432 | 11/1989 | Abou-Gharbia | 544/360 |
| 4,988,814 | 1/1991 | Abou-Gharbia et al. | 544/360 |
| 5,106,849 | 4/1992 | Abou-Gharbia et al. | 514/252 |

FOREIGN PATENT DOCUMENTS

879102 8/1971 Canada.
48045 3/1982 European Pat. Off..
0138280 4/1985 European Pat. Off..
2218988 11/1989 United Kingdom.

OTHER PUBLICATIONS

Chem. Abstr. Index Guide 1982–1986 p. 1189G (1987).
Chem. Abstr. Skwarski et al., vol. III, No. 57109 (1988).
Chem. Abstr. Lattrell et al., vol. 87, No. 117777 (1977).
Chem. Abstr. Arava et al., vol. 78, No. 83900 (1972).

*Primary Examiner*—Emily Bernhardt
*Attorney, Agent, or Firm*—Walter Patton

[57] ABSTRACT

There are disclosed compounds of the formula (I)

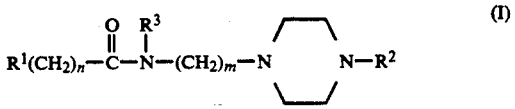

wherein $R^1$ is 1-adamantyl, 3-methyl-1-adamantyl, 3-noradamantyl, unsubstituted or substituted-2-indolyl, 3-indolyl, 2-benzofuranyl and 3-benzofuranyl wherein the substituents are selected from lower alkyl, lower alkoxy and halo; $R^2$ is unsubstituted or substituted phenyl, benzyl, pyridinyl, pyrimidinyl or pyrazinyl, wherein the substituents are selected from lower alkyl, lower alkoxy, trifluoromethyl and halo; $R^3$ is H or lower alkyl of 1 to 3 carbon atoms; n is the integer 0 or 1; m is the integer from 2 to 5; and the pharmaceutically acceptable salts thereof.

The compounds of this invention which demonstrate selectivity at the 5-HT$_{1A}$ and 5-HT$_2$ versus D$_2$ receptor binding sites are useful as potential anxiolytic-antidepressant agents.

Compounds of this invention with equal high affinity for the 5-HT$_{1A}$ and D$_2$-receptor binding sites are useful as mixed antipsychotic-anxiolytic agents.

Compounds of this invention which demonstrate central cholinergic activity are useful in the treatment of senile dementia of the Alzheimer type (SDAT) and Huntingdon's chorea.

3 Claims, No Drawings

ARYL-AND HETEROARYL PIPERAZINYL CARBOXAMIDES HAVING CENTRAL NERVOUS SYSTEM ACTIVITY

This is a continuation application of U.S. Ser. No. 533,974, filed Jun. 6, 1990, now abandoned, which is a divisional application of copending U.S. Ser. No. 07/493,179, filed Mar. 14, 1990 and issued as U.S. Pat. No. 5,010,078 which is a continuation-in-part application of copending U.S. Ser. No. 335,075, filed Apr. 7, 1989, now abandoned, which is in turn a continuation-in-part application of copending U.S. Ser. No. 297,460, filed Jan. 13, 1989, now abandoned, which is in turn a continuation-in-part application of copending U.S. Ser. No. 197,890, filed May 24, 1988, now abandoned.

The recent introduction of buspirone having a selecting for 5-HT$_{1A}$ receptors, as an effective anxiolytic agent U.S. Pat. No. 3,717,634, into the United States marketplace has stimulated interest in development of second generation anxiolytic agents.

Furthermore, in clinical trials, gepirone and ipsapirone were found to be potent anxiolytic drugs. Since both drugs—gepirone and ipsapirone—possess a higher degree of selectivity for 5-HT$_{1A}$ receptors than buspirone, the clinical data support the notion that anxiety mechanisms can directly be modulated by 5-HT$_{1A}$ receptor drug interactions.

In addition to treatment of anxiety, 5-HT$_{1A}$ agonists such as gepirone are now being examined for their mixed activity as anxiolytic antidepressant agents. The therapeutic potential of 5-HT$_{1A}$ agonists in the treatment of multi-CNS disorders was recently extended to the development of antipsychotic anxiolytic agents represented by MDL-72832 and KC-9172 (Br. J. Pharmocol., 90, 273P, 1987), the latter being under development as an antipsychotic agent (Scrip No. 1265, Dec. 11, 1987). This class of compounds demonstrated high affinity for both the 5-HT$_{1A}$ and D$_2$ receptor binding sites.

U.S. Pat. No. 4,202,898 describes arylpiperazines useful for the treatment of anxiety and depression. U.S. Pat. No. 4,001,223 describes the synthesis of adamantane derivatives useful as cerebral vasodilators. Abou-Gharbia et al, U.S. Pat. No. 4,797,489, describes the synthesis of adamantyl and fluorenylarylpiperazines with potential CNS activity.

U.S. Pat. No. 4,202,898 discloses synthesis of arylpiperazines of the general formula

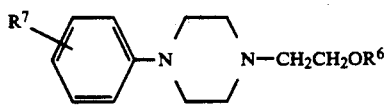

wherein R$^6$ is H, CO (lower alkyl), CO (monocyclic aryl), CONH (lower alkyl), CON (lower alkyl) or CONH (monocyclic aryl); R$^7$ is H, alkyl, alkoxy, CN, halo or trifluoromethyl useful for the treatment of anxiety and depression.

Compounds of the present invention differ in having a substituted adamantyl, noradamantyl, indolyl or benzofuryl amide moiety attached to the alkylarylpiperazinyl functionality.

The present invention relates to novel carboxamides having CNS activity and being characterized by the general formula

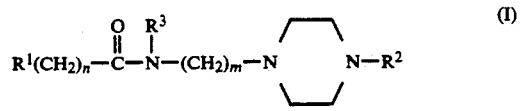

wherein R$^1$ is 1-adamantyl, 3-methyl-1-adamantyl, 3-noradamantyl, unsubstituted or substituted-2-indolyl, 3-indolyl, 2-benzofuranyl or 3-benzofuranyl wherein the substituents are selected from lower alkyl, lower alkoxy and halo; R$^2$ is unsubstituted or substituted phenyl, benzyl, pyridinyl, pyrimidinyl or pyrazinyl, wherein the substituents are selected from lower alkyl, lower alkoxy, trifluoromethyl and halo; R$^3$ is H or lower alkyl of 1 to 3 carbon atoms; n is the integer 0 or 1; and m is the integer from 2 to 5 and the pharmaceutically acceptable salts thereof.

The most preferred compounds of the present invention are designated:

N-[3-[4-(2-methoxyphenyl)-1-piperazinyl]propyl]tricyclo[3.3.1.1$^{3,7}$]decane-1-carboxamide;
N-[2-[4-(2-pyrimidinyl)-1-piperazinyl]ethyl]tricyclo[3.3.1.1$^{3,7}$]decane-1-carboxamide;
N-[2-[4-(2-methoxyphenyl)-1-piperazinyl]ethyl]tricyclo[3.3.1.1$^{3,7}$]decane-1-carboxamide;
N-[2-[4-(3-chlorophenyl)-1-piperazinyl]ethyl]tricyclo[3.3.1.1$^{3,7}$]decane-1-carboxamide;
N-[2-[4-(2-pyrimidinyl)-1-piperazinyl]ethyl]-2-benzofurancarboxamide;
N-[3-[4-(2-methoxyphenyl)-1-piperazinyl]propyl]-2-benzofurancarboxamide;
N-[3-[4-(2-methoxyphenyl)-1-piperazinyl]propyl]-1H-indole-2-carboxamide;
N-[3-[4-(3-chlorophenyl)-1-piperazinyl]propyl]tricyclo[3.3.1.1$^{3,7}$]decane-1-carboxamide;
N-[2-[4-(2-pyrimidinyl)-1-piperazinyl]ethyl]-3-methyltricyclo[3.3.1.1$^{3,7}$]decane-1-acetamide;
N-[3-[4-(2-pyrimidinyl)-1-piperazinyl]propyl]tricyclo[3.3.1.1$^{3,7}$]decane-1-carboxamide;
N-[2-[4-(3-chlorophenyl)-1-piperazinyl]ethyl]-3-methyltricyclo[3.3.1.1$^{3,7}$]decane-1-acetamide;
N-[2-[4-(2-methoxyphenyl)-1-piperazinyl]ethyl]-3-methyltricyclo[3.3.1.1$^{3,7}$]decane-1-acetamide; N-[2-[4-(2-pyrimidinyl)-1-piperazinyl]ethyl]hexahydro-2,5-methanopentalene-3a(1H)-carboxamide;
N-[2-[4-(2-methoxyphenyl)-1-piperazinyl]ethyl]hexahydro-2,5-methanopentalene-3a(1H)-carboxamide;
N-[2-[4-(3-chlorophenyl)-1-piperazinyl]ethyl]hexahydro-2,5-methanopentalene-3a(1H)-carboxamide;
N-[2-[4-[3-(trifluoromethyl)phenyl]-1-piperazinyl]ethyl]hexahydro-2,5-methanopentalene-3a(1H)-carboxamide;
N-[3-[4-(2-pyrimidinyl)-1-piperazinyl]propyl]hexahydro-2,5-methanopentalene-3a(1H)-carboxamide;
N-[3-[4-(2-methoxyphenyl)-1-piperazinyl]propyl]hexahydro-2,5-methanopentalene-3a(1H)-carboxamide;
N-[3-[4-(3-chlorophenyl)-1-piperazinyl]propyl]hexahydro-2,5-methanopentalene-3a(1H)-carboxamide;
and the pharmaceutically acceptable salts thereof.

The term "lower alkyl" refers to moieties having 1 to 6 carbon atoms in the carbon chain. The term "alkoxy" refers to moieties having 1 to 6 carbon atoms. The term "halo" refers to fluoro, chloro and bromo.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of this invention which demonstrated selectivity at the 5-$HT_{1A}$ and 5-$HT_2$ versus $D_2$ receptor binding sites are useful as potential anxiolytic-antidepressant agents.

In addition, compounds of this invention with equal high affinity for the 5-$HT_{1A}$ and $D_2$-receptor binding sites are useful as mixed antipsychotic-anxiolytic agents.

Compounds of this invention which demonstrated central cholinergic activity could be useful in the treatment of senile dementia of the Alzheimer type (SDAT) and Huntingdon's chorea.

Compounds of this invention can be prepared by a variety of synthetic routes by building the molecule up from smaller constituent molecules.

Accordingly this invention provides a process for preparing a compound of formula (I) as defined above which comprises one of the following:

(a) acylating a compound of formula

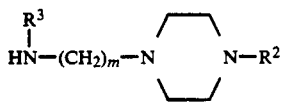  (III)

with an acylating agent containing the group $R^5$ wherein $R^5$ is:

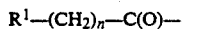  (IIa)

wherein n, m, $R^1$, $R^2$, and $R^3$ are as defined above to give a compound of formula (I); or (b) a cyclic amine having the formula (IV)

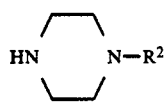  (IV)

wherein $R^2$ is as defined above or a salt thereof is alkylated to introduce the substituted alkyl group having the formula (V)

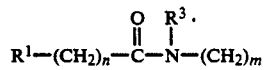  (V)

by reaction with a compound having the formula $R^4$—Y (wherein $R^4$ is the group having formula (V) and Y is a leaving group, for example halo such as chloro or bromo or aryl- or alkylsulphonyloxy); or (c) a cyclic amine having the formula (IV) as defined above or a salt thereof is subjected to reductive alkylation with an aldehyde having the formula (VI)

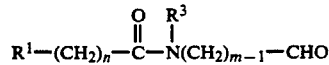  (VI)

wherein n, $R^1$, $R^3$ and m are as defined above; or (d) a compound having formula (I) is converted into an acid addition salt thereof by addition of an acid or an acid addition salt of a compound having formula (I) is subjected to neutralisation to form the compound having formula (I).

With reference to process step (a) above, acylation is conveniently carried out under basic conditions using methods generally known for preparing secondary or tertiary amides. Examples of acylating agents are reactive derivatives of acids of formula $R^5OH$ such as acid halides, e.g. the chloride, azide, anhydride, mixed anhydride (e.g. formed with carbonyldiimidazole) or activated esters (e.g. 1-benzotriazolyl,2,3,4-trichlorophenyl or p-nitrophenyl) or O-acyl ureas obtained from carbodiimides such as dialkylcarbodiimides, e.g. dicyclohexylcarbodiimide. Descriptions of methods for forming amides are given in the literature—see for example "The Chemistry of Amides" Interscience Publisher, 1970. Chapter beginning at p 73 from the series "The Chemistry of Functional Groups" edited by Saul Patai and books on peptide chemistry—e.g. "The Practice of Peptide Synthesis" by M. Bodanszky and A. Bodanszky, Springer Verlag, 1984. Volume 21 of the series "Reactivity and Structure Concepts in Organic Chemistry."

Process step (b) may be carried out in the conventional manner for the preparation of tertiary amines by alkylation of secondary amines. In particular the reaction may be carried out in a suitable solvent, e.g. dimethylformamide in the presence of an inorganic base or a tertiary amine, e.g. triethylamine.

Process step (c) may be carried out in the conventional manner for the preparation of tertiary amines from secondary amines and aldehydes by reductive alkylation. The reductive alkylation may be carried out with hydrogen and platinum catalyst or using sodium cyanoborohydride.

Starting materials for the processes described above are in general known compounds or can be prepared by methods known for analogous compounds where necessary by building up the molecule from readily available starting materials.

Piperazines of formula (IV) can be prepared by known methods, e.g. reaction of bis-(2-chloroethyl)amine with an amine or aniline of formula $H_2NR^2$.

Compounds of formula $R^4$—Y wherein $R^4$ is

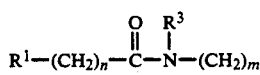  (V)

can be prepared by (a) acylating an hydroxy amine of formula $HR^3N$—$(CH_2)_mOH$ with an acylating agent containing the group

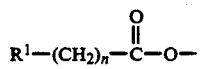  (IIa)

to give a compound of formula $R^4OH$ and (b) converting the terminal OH group to a leaving group by known methods, e.g. halogenating (using $SOCl_2$) or sulphonating. Compounds of formula (VI) may be prepared by oxidising compounds of formula $R^4OH$, e.g. using pyridinium chlorochromate in dichloromethane.

In a preferred process 1-adamantane carboxylic acid halide, noradamantane carboxylic acid halide, indolecarboxylic acid halide or benzofurancarboxylic acid halide of formula (II) may be conveniently reacted with the appropriately substituted aminoalkyl piperazine of formula (III)

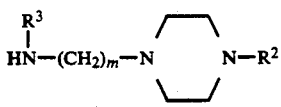

in CH$_2$Cl$_2$ and the presence of a suitable base, such as triethylamine, to obtain the desired final product (I).

Scheme 1

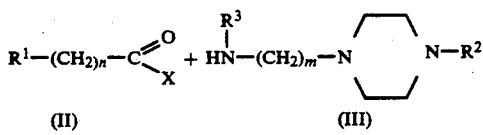

wherein X is a halide and R$^1$, R$^2$, and R$^3$, m, and n are as defined above. For the particular case when R$^2$ is benzyl, hydrogenation of (I) followed by treatment of the product R$^2$ is H with 2-chloropyrimidine permits an alternative synthesis of (I) where R$^2$ is 2-pyrimidinyl.

Of course, other methods of preparation, which will occur to those skilled in the art, may also be employed to prepare the compounds of the invention.

The starting material used in the above-described preparative routes are commercially available, or can be made according to procedures taught in the chemical literature.

The compounds of the invention may exist either in the form of the free base or the pharmacologically acceptable salts. Methods for converting one such form to another will be obvious to one skilled in the chemical arts.

The compounds of the invention display a preclinical pharmacological profile like that of the compound gepirone (4,4-dimethyl-1-[4-[4-(2-pyrimidinyl)-1-piperazinyl]butyl]-2,6-piperidinedione) and ritanserin 6-[2-[4-[bis(4-fluorophenyl)methylene]-1-piperidinyl]-7-methyl-5H-thiazolo[3,2-a]pyrimidin-5-one. Gepirone and ritanserin have demonstrated clinical activity in anxiolytic and antidepressant paradigms and have also displayed a unique clinical anxio- selective profile, whereby their efficacy in the treatment of anxiety neuroses is comparable to the benzodiazepine diazepam. The compounds of the invention, in a manner similar to ritanserin and gepirone, may also display preclinical anxiolytic and antidepressant activities with expected minimal side effects. The compounds of the invention also demonstrate a pharmacological profile similar to the nonbenzodiazepine anxiolytic buspirone, which also supports their use in anxiety neurosis. Moreover, based on the central cholinergic activity, some of the compounds of the present invention are useful in the treatment of central cholinergic dysfunction attending senile dementia of the Alzheimer type (SDAT).

When employed as anxiolytic/antidepressant, the effective dosage of the active substances for such treatment will vary according to the particular compound being employed, and the severity and nature of the condition being treated. Therapy should be initiated at lower doses, the dosage thereafter being increased, if necessary, to produce the desired effect. In general, the compounds of the invention are most desirably administered at a concentration that will generally afford effective results without causing any harmful or deleterious side effects.

When the compounds of the invention are employed as anxiolytic/antidepressant or anxiolytic/antipsychotic agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be sufficient at least to impart the desired activity thereto on oral administration. The compounds may also be injected parenterally in which case they are used in the form of a sterile solution containing other solutes, for example, enough saline or glucose to make the solution isotonic. Accordingly, this invention provides a pharmaceutical composition comprising a compound of formula (I) or a pharmaceutically acceptable salt thereof and a pharmaceutically acceptable carrier. The antidepressant activity of the compounds of the invention and their expected lack of extrapyramidal side effects may be demonstrated by standard pharmacological procedures, which are described more fully in the examples given hereafter.

The following examples show the preparation and pharmacological testing of compounds within the invention.

EXAMPLE 1

N-[3-[4-(2-Methoxyphenyl)-1-piperazinyl]propyl]tricyclo[3.3.1.1$^{3,7}$]decane-1-carboxamide Hydrochloride Hemihydrate To a stirred solution of [4-(2-methoxyphenyl)-piperazino]propylamine (2.5 g, 0.01 mol) in 50 mL of methylene chloride, adamantane-1-carboxylic acid chloride (2.02 g, 0.010 mol) and triethylamine (2 g, 0.02 mol) were added. Stirring was continued at room temperature overnight. The methylene chloride solution was washed with water, dried over anhydrous sodium sulfate and evaporated under reduced pressure. The remaining residue was subjected to preparative HPLC. In repeated preparations, the residue was dissolved in ethyl acetate (10 mL) and subjected to flash chromatography using a 9 inch column of silica gel and ethyl acetate as the eluent. The title compound (TLC R$_f$=0.53 in 30% methanol/ethyl acetate system) was separated and converted to the hydrochloride hemihydrate salt with ethanolic HCl (2.3 g), m.p. 186°–190° C.

Anal. Calcd. C$_{25}$H$_{37}$N$_3$O$_2$.HCl.0.5H$_2$O: C, 65.69; H, 8.60; N, 9.19%. Found: C, 66.04; H, 8.26; N, 9.18%.

EXAMPLE 2

N-[2-[4-(2-Pyrimidinyl)-1-piperazinyl]ethyl]tricyclo[3.3.1.1$^{3,7}$]decane-1-carboxamide Dihydrochloride Hydrate To a stirred solution of [4-(2-pyrimidinyl)-piperazino]ethylamine (2.0 g, 0.01 mol) in 50 mL of methylene chloride, adamantane-1-carboxylic acid chloride (3.6 g, 0.018 mol) and triethylamine (2.9 g, 0.015 mol) were added. Stirring was continued at room temperature overnight. The methylene chloride solution was washed with water, dried over anhydrous sodium sulfate and evaporated under reduced pressure. The remaining residue was dissolved in ethyl acetate (10 mL) and subjected to column chromatography using silica gel and ethyl acetate as the eluent. The title compound was separated and converted to the dihydrochloride hydrate salt with ethanolic HCl (2.4 g), m.p. 237°–239° C.

Anal. Calcd. $C_{21}H_{31}N_5O.2HCl.H_2O$: C, 54.80; H, 7.66; N, 15.21%. Found: C, 54.99; H, 6.91; N, 15.14%.

EXAMPLE 3

N-[2-[4-(2-Methoxyphenyl)-1-piperazinyl]ethyl]tricyclo[3.3.1.1$^{3,7}$]decane-1-carboxamide Dihydrochloride Three-Quarters Hydrate To a stirred solution of [4-(2-methoxyphenyl)-piperazino]ethylamine (2.53 g, 0.01 mol) in 50 mL of methylene chloride, adamantane-1-carboxylic acid chloride (3 g, 0.02 mol) and triethylamine (2 g, 0.02 mol) were added. Stirring was continued at room temperature overnight. The methylene chloride solution was washed with water, dried over anhydrous sodium sulfate and evaporated under reduced pressure. The remaining residue was subjected to preparative HPLC. In repeated preparations, the residue was dissolved in ethyl acetate (10 mL) and subjected to flash chromatography using a 9 inch column of silica gel and ethyl acetate as the eluent. The title compound (TLC $R_f=0.65$ in 30% methanol/ethyl acetate system) was separated and converted to the dihydrochloride three-quarters hydrate salt with ethanolic HCl (1.6 g), m.p. 206°–212° C.

Anal. Calcd. $C_{24}H_{35}N_3O_2.2HCl.0.75H_2O$: C, 59.56; H, 8.02; N, 8.68%. Found: C, 59.65; H, 7.38; N, 8.65%.

EXAMPLE 4

N-[2-[4-(3-Chlorophenyl)-1-piperazinyl]ethyl]tricyclo[3.3.1.1$^{3,7}$]decane-1-carboxamide Dihydrochloride To a stirred solution of [4-(m-chlorophenyl)-piperazino]ethylamine (2.5 g, 0.01 mol) in 50 mL of methylene chloride, adamantane-1-carboxylic acid chloride (5 g, 0.018 mol) and triethylamine (3.6 g, 0.018 mol) were added. Stirring was continued at room temperature overnight. The methylene chloride solution was washed with water, dried over anhydrous sodium sulfate and evaporated under reduced pressure. The remaining residue was dissolved in ethyl acetate (10 mL) and subjected to column chromatography using silica gel and ethyl acetate as the eluent. The title compound was separated and converted to the dihydrochloride salt with ethanolic HCl (0.7 g), m.p. 210°–213° C.

Anal. Calcd. $C_{23}H_{32}ClN_3O.2HCl$: C, 58.17; H, 7.22; N, 8.45%. Found: C, 57.70; H, 7.02; N, 8.61%.

EXAMPLE 5

N-[2-[4-(2-Pyrimidinyl)-1-piperazinyl]ethyl]-2-benzofurancarboxamide Dihydrochloride Hydrate To a stirred solution of [4-(2-pyrimidinyl)-piperazino]ethylamine (2.0 g, 0.01 mol) in 50 mL of methylene chloride, benzofurane-2-carboxylic acid chloride (2.6 g, 0.014 mol) and triethylamine (2 g, 0.02 mol) were added. Stirring was continued at room temperature overnight. The methylene chloride solution was washed with water, dried over anhydrous sodium sulfate and evaporated under reduced pressure. The remaining residue was subjected to preparative HPLC. The title compound was separated and converted to the dihydrochloride hydrate salt with ethanolic HCl (0.5 g), m.p. 193° C.

Anal. Calcd. $C_{19}H_{21}N_5O_2.2HCl.H_2O$: C, 51.59; H, 5.70; N, 15.83%. Found: C, 51.42; H, 5.50; N, 15.71%.

EXAMPLE 6

N-[3-[4-(2-Methoxyphenyl)-1-piperazinyl]propyl]-2-benzofurancarboxamide Dihydrochloride To a stirred solution of [4-(2-methoxyphenyl)-piperazino]propylamine (1.0 g, 0.04 mol) in 50 mL of methylene dichloride, benzofurane-2-carboxylic acid chloride (1.01 g, 0.0056 mol) and triethylamine (1 g, 0.01 mol) were added. Stirring was continued at room temperature overnight. The methylene chloride solution was washed with water, dried over anhydrous sodium sulfate and evaporated under reduced pressure. The remaining residue was subjected to preparative HPLC using silica gel column and ethyl acetate as the eluent. The title compound was separated and converted to the dihydrochloride salt with ethanolic HCl (0.9 g), m.p. 228°–232° C.

Anal. Calcd. $C_{23}H_{27}N_3O_3.2HCl$: C, 59.23; H, 6.27; N, 9.01%. Found: C, 59.59; N, 6.12; N, 8.84%.

EXAMPLE 7

N-[3-[4-(2-Methoxyphenyl)-1-piperazinyl]propyl]-1H-indole-2-carboxamide Dihydrochloride Dihydrate The title compound was prepared by stirring [4-(2-methoxyphenyl)piperazino]propylamine (1.4 g, 0.005 mol), indole-2-carboxylic acid chloride (1.0 g, 0.005 mol) and triethylamine (1 g, 0.01 mol) in 50 mL of $CH_2Cl_2$ for 24 hours. The methylene chloride solution was washed with water, dried (anhydrous $Na_2SO_4$) and evaporated under reduced pressure. The remaining residue was subjected to preparative HPLC over silica gel column and using ethyl acetate as the eluent and the desired product (TLC $R_f=0.65$ in 30% methanol/ethyl acetate system) was separated and converted to the dihydrochloride dihydrate salt with ethanolic HCl, m.p. 173°–178° C.

Anal. Calcd. $C_{23}H_{28}N_4O_2.2HCl.2H_2O$: C, 55.49; H, 6.41; N, 10.73%. Found: C, 55.09; H, 6.83; N, 11.17%.

EXAMPLE 8

N-[3-[4-(3-Chlorophenyl)-1-piperazinyl]propyl]tricyclo[3,3,1,1$^{3,7}$]decane-1-carboxamide Dihydrochloride One and One-half Hydrate To a stirred solution of [4-(3-chlorophenyl)-piperazino]propylamine (1.28 g, 0.005 mol) in 50 mL of methylene chloride, adamantane-1-carboxylic acid chloride (1 g, 0.005 mol) and triethylamine (1 g, 0.01 mol) were added. Stirring was continued at room temperature overnight. The methylene chloride solution was washed with water, dried over anhydrous sodium sulfate and evaporated under reduced pressure. The remaining residue was subjected to preparative HPLC using silica gel column and ethyl acetate as the eluent. The title compound was separated and converted to the dihydrochloride salt with ethanolic HCl (1.5 g), m.p. 209°–210° C.

Anal. Calcd. $C_{24}H_{34}ClN_3O.2HCl.1.50H_2O$: C, 55.87; H, 4.72; N, 8.14%. Found: C, 56.05; H, 7.62; N, 7.69%.

EXAMPLE 9

N-[2-[4-(2-Pyrimidinyl)-1-piperazinyl]ethyl]-3-methyl-tricyclo[3,3,1,1$^{3,7}$]decane-1-acetamide Dihydrochloride Hemihydrate The title compound was prepared by stirring [4-(2-pyrimidinyl]piperazino]ethylamine (2.0 g, 0.009 mol), 3-methyladamantane-1-acetic acid bromoethyl ester (2.34 g, 0.01 mol) and triethylamine (1.0 g, 0.015 mol) in 50 mL of CH$_2$Cl$_2$ for 24 hours. The methylene chloride solution was washed with water, dried (anhydrous Na$_2$SO$_4$) and removed under reduced pressure. The remaining residue was subjected to preparative HPLC over silica gel column using ethyl acetate as the eluent and the desired product was separated and converted to the dihydrochloride hemihydrate salt with ethanolic HCl, m.p. 248°-251° C.

Anal. Calcd. C$_{23}$H$_{34}$N$_5$O.2HCl.0.50H$_2$O: C, 57.61; H, 7.99; N, 14.61%. Found: C, 57.08; H, 7.70; N, 14.39%.

EXAMPLE 10

N-[3-[4-(2-Pyrimidinyl)-1-piperazinyl]propyl]tricyclo[3,3,1,1$^{3,7}$]decane-1-carboxamide Hydrochloride Hydrate To a stirred solution of [4-(2-pyrimidinyl)piperazino]propylamine (1.12 g, 0.005 mol) in 50 mL of methylene chloride, adamantane-1-carboxylic acid chloride (1 g, 0.005 mol) and triethylamine (1.0 g, 0.01 mol) were added. Stirring was continued at room temperature overnight. The methylene chloride solution was washed with water, dried over anhydrous sodium sulfate and evaporated under reduced pressure. The remaining residue was subjected to preparative HPLC using a column of silica gel and ethyl acetate as the eluent. The title compound was separated and converted to the hydrochloride hydrate salt with ethanolic HCl (1.6 g), m.p. 146°-148° C.

Anal. Calcd. C$_{22}$H$_{33}$N$_5$O.HCl.H$_2$O: C, 60.32; H, 8.29; N, 15.99%. Found: C, 60.57; H, 8.49; N, 15.10%.

EXAMPLE 11

N-[2-[4-(3-Chlorophenyl)-1-piperazinyl]ethyl]-3-methyltricyclo[3,3,1,1$^{3,7}$]decane-1-acetamide Dihydrochloride Two and One-half Hydrate The title compound was prepared by stirring [4-(3-chlorophenyl)piperazinyl]ethylamine (2.5 g, 0.010 mol), 3-methyladamantane-1-acetic acid bromoethyl ester (2.67 g, 0.01 mol) and triethylamine (2 g, 0.025 mol) in 50 mL of CH$_2$Cl$_2$ for 24 hours. The methylene chloride solution was washed with water, dried (anhydrous Na$_2$SO$_4$) and evaporated under reduced pressure. The remaining residue was subjected to preparative HPLC over silica gel using ethyl acetate as the eluent and the desired product was separated and converted to the dihydrochloride, 2½ hydrate salt with ethanolic HCl, m.p. 178°-182° C.

Anal. Calcd. C$_{25}$H$_{36}$ClN$_3$O.2HCl.2.50H$_2$O: C, 54.80; H, 7.91; N, 7.67%. Found: C, 54.44; H, 6.97; N, 7.49%.

EXAMPLE 12

N-[2-[4-(2-Methoxyphenyl)-1-piperazinyl]ethyl]-3-methyltricyclo]3,3,1,1$^{3,7}$]decane-1-acetamide Dihydrochloride To a stirred solution of [4-(2-methoxyphenyl)-piperazino]ethylamine (2.0 g, 0.008 mol) in 50 mL of methylene chloride, 3-methyladamantane-1-carboxylic acid chloride (2.1 g, 0.004 mol) and triethylamine (1 g, 0.01 mol) were added. Stirring was continued at room temperature overnight. The methylene chloride solution was washed with water, dried over anhydrous sodium sulfate and evaporated under reduced pressure. The remaining residue was subjected to preparative HPLC using a column of silica gel and ethyl acetate as the eluent. The title compound was separated and converted to the dihydrochloride salt with ethanolic HCl (1.3 g), m.p. 194°-197° C.

Anal. Calcd. C$_{26}$H$_{39}$N$_3$O$_2$.2HCl: C, 62.64; H, 8.29; N, 8.43%. Found: C, 62.07; H, 7.75; N, 8.76%.

EXAMPLE 13

N-[2-[4-(2-Pyrimidinyl)-1-piperazinyl]ethyl]hexahydro-2,5-methanopentalene-3a(1H)-carboxamide Dihydrochloride Hemihydrate To a stirred solution of noradamantane-3-carboxylic acid (0.6 g, 3.6×10$^{-3}$ mol) in 25 mL of chloroform under a dry nitrogen atmosphere was added carbonyldiimidazole (0.58 g, 3.6×10$^{-3}$ mol). The resulting solution was stirred at ambient temperature for three hours, during which time a gas (CO$_2$) was evolved. A solution of 2-[1-(2-pyrimidinyl)-4-piperazinyl]aminoethane (0.75 g, 3.6×10$^{-3}$ mol) in 25 mL of chloroform was then added, and the resulting reaction mixture was stirred under nitrogen at ambient temperature for 2 days. The mixture was diluted to 150 mL with chloroform, washed with three-one hundred mL portions of water, dried over anhydrous sodium sulfate, and concentrated on a rotary evaporator. The desired product (TLC on silica using a 30% methanol in ethyl acetate solvent system, R$_f$=0.45) was isolated by gravity chromatography on silica gel and converted to the dihydrochloride hemihydrate salt (0.84 g, 50% yield), m.p. 210°-211° C.

Anal. Calcd. C$_{20}$H$_{29}$N$_5$O.2HCl.0.50H$_2$O: C, 54.87: H, 7.36: N, 16.00%. Found: C, 54.69; H, 7.13; N, 16.56%.

EXAMPLE 14

N-[2-[4-(2-Methoxyphenyl)-1-piperazinyl]ethyl]hexahydro-2,5methanopentalene-3a(1H)-carboxamide Dihydrochloride To a stirred solution of noradamantane-3-carboxylic acid (0.6 g, 3.6×10$^{-3}$ mol) in 25 mL of chloroform under a dry nitrogen atmosphere was added carbonyldiimidazole (0.58 g, 3.6×10$^{-3}$ mol). The resulting solution was stirred at ambient temperature for three hours during which time a gas (CO$_2$) was evolved. A solution of 2-[1-(2-methoxyphenyl)-4-piperazinyl]aminoethane (0.85 g, 3.6×10$^{-3}$ mol) in 25 mL of chloroform was then added, and the resulting reaction mixture was stirred under nitrogen at ambient temperature for 2 days. The mixture was diluted to 150 mL with chloroform, washed with three-one hundred mL portions of water, dried over anhydrous sodium sulfate, and concentrated on a rotary evaporator. The desired product (TLC on silica using a 20% methanol in ethyl acetate solvent system, R$_f$=0.47) was isolated by gravity chromatography on silica gel and converted to the dihydrochloride salt (0.84 g, 56% yield), m.p. 192°-193° C.

Anal. Calcd. C$_{23}$H$_{33}$N$_3$O$_2$.2HCl: C, 60.46; H, 7.66; N, 9.20%, Found: C, 60.06; H, 7.48; N, 9.14%.

EXAMPLE 15

N-[2-[4-(3-Chlorophenyl)-1-piperazinyl]ethyl]hexahydro-2,5-methanopentalene-3a(1H)-carboxamide Dihydrochloride To a stirred solution of noradamantane-3-carboxylic acid (0.6 g, $3.6 \times 10^{-3}$ mol) in 25 mL of chloroform under a dry nitrogen atmosphere was added carbonyldiimidazole (0.58 g, $3.6 \times 10^{-3}$ mol). The resulting solution was stirred at ambient temperature for three hours, during which time a gas ($CO_2$) was evolved. A solution of 2-[1-(3-chlorophenyl)-4-piperazinyl]aminoethane (0.86 g, $3.6 \times 10^{-3}$ mol) in 25 mL of chloroform was then added, and the resulting mixture was stirred under nitrogen at ambient temperature for 2 days. The mixture was diluted to 150 mL with chloroform, washed with three-one hundred mL portions of water, dried over anhydrous sodium sulfate, and concentrated on a rotary evaporator. The desired product (TLC on silica using a 20% methanol in ethyl acetate solvent system, $R_f = 0.55$) was isolated by gravity chromatography on silica gel and converted to the dihydrochloride salt (0.75 g, 43% yield), m.p. 226°-227° C.

Anal. Calcd. $C_{22}H_{30}ClN_3O \cdot 2HCl$: C, 57.33; H, 6.99; N, 9.12%, Found: C, 57.58; H, 7.10; N, 9.12%.

EXAMPLE 16

N-[2-[4-[3-(Trifluoromethyl)phenyl]-1-piperazinyl]ethyl]hexahydro-2,5-methanopentalene-3a(1H)-carboxamide Dihydrochloride To a stirred solution of noradamantane-3-carboxylic acid (0.6 g, $3.6 \times 10^{-3}$ mol) in 25 mL of chloroform under a dry nitrogen atmosphere was added carbonyldiimidazole (0.58 g, $3.6 \times 10^{-3}$ mol). The resulting solution was stirred at ambient temperature for three hours, during which time a gas ($CO_2$) was evolved. A solution of 2-[1-(3-chlorophenyl)-4-piperazinyl]aminoethane (0.98 g, $3.6 \times 10^{-3}$ mol) in 25 mL of chloroform was then added, and the resulting reaction mixture was stirred under nitrogen at ambient temperature for 2 days. The mixture was diluted to 150 mL with chloroform, washed with three-one hundred mL portions of water, dried over anhydrous sodium sulfate, and concentrated on a rotary evaporator. The desired product (TLC on silica using a 10% methanol in ethyl acetate solvent system, $R_f = 0.40$) was isolated by preparative high pressure liquid chromatography (HPLC) on silica gel using a 0% to 5% gradient of methanol in ethyl acetate, and converted to the dihydrochloride salt (0.88 g, 50% yield), m.p. 222°-223° C.

Anal. Calcd. $C_{23}H_{30}F_3N_3O \cdot 2HCl$: C, 55.87; H, 6.52; N, 8.50%, Found: C, 56.12; H, 6.90; N, 8.42%.

EXAMPLE 17

N-[3-[4-(2-Pyrimidinyl)-1-piperazinyl]propyl]hexahydro-2,5-methanopentalene-3a(1H)-carboxamide Dihydrochloride To a stirred solution of noradamantane-3-carboxylic acid (0.6 g, $3.6 \times 10^{-3}$ mol) in 25 mL of chloroform under a dry nitrogen atmosphere was added carbonyldiimidazole (0.58 g, $3.6 \times 10^{-3}$ mol). The resulting solution was stirred at ambient temperature for three hours, during which time a gas ($CO_2$) was evolved. A solution of 3-[1-(2-pyrimidinyl)-4-piperazinyl]aminopropane (0.80 g, $3.6 \times 10^{-3}$ mol) in 25 mL of chloroform was then added, and the resulting reaction mixture was stirred under nitrogen at ambient temperature for 2 days. The mixture was diluted to 150 mL with chloroform, washed with three-one hundred mL portions of water, dried over anhydrous sodium sulfate, and concentrated on a rotary evaporator. The desired product (TLC on silica using a 30% methanol in ethyl acetate solvent system, $R_f = 0.44$) was isolated by preparative HPLC on silica gel using a 2% to 5% gradient of methanol in ethyl acetate, and converted to the dihydrochloride salt (0.65 g, 42% yield), m.p. 229°-230° C.

Anal. Calcd. $C_{21}H_{31}N_5O \cdot 2HCl$: C, 57.01; H, 7.52; N, 15.83%, Found: C, 56.64; H, 7.51; N, 51.49%.

EXAMPLE 18

N-[3-[4-(2-Methoxyphenyl)-1-piperazinyl]propyl]hexahydro-2,5-methanopentalene-3a(1H)-carboxamide Dihydrochloride To a stirred solution of noradamantane-3-carboxylic acid (0.6 g, $3.6 \times 10^{-3}$ mol) in 25 mL of chloroform under a dry nitrogen atmosphere was added carbonyldiimidazole (0.58 g, $3.6 \times 10^{-3}$ mol). The resulting solution was stirred at ambient temperature for three hours, during which time a gas ($CO_2$) was evolved. A solution of 3-[1-(2-methoxyphenyl)-4-piperazinyl]aminopropane (0.91 g, $3.6 \times 10^{-3}$ mol) in 25 mL of chloroform was then added, and the resulting reaction mixture was stirred under nitrogen at ambient temperature for 2 days. The mixture was diluted to 150 mL with chloroform, washed with three-one hundred mL portions of water, dried over anhydrous sodium sulfate, and concentrated on a rotary evaporator. The desired product (TLC on silica using a 30% methanol in ethyl acetate solvent system, $R_f = 0.45$) was isolated by gravity chromatography on silica gel and converted to the dihydrochloride salt (0.96 g, 56% yield), m.p. 201°-202° C.

Anal. Calcd. $C_{24}H_{35}N_3O_2 \cdot 2HCl$: C, 61.27; H, 7.93; N, 8.93%, Found: C, 60.88; H. 7.81; N, 8.81%.

EXAMPLE 19

N-[3-[4-(3-Chlorophenyl)-1-piperazinyl]propyl]hexahydro-2,5-methanopentalene-3a(1H)-carboxamide Hydrochloride To a stirred solution of noradamantane-3-carboxylic acid (0.6 g, $3.6 \times 10^{-3}$ mol) in 25 mL of chloroform under a dry nitrogen atmosphere was added carbonyldiimidazole (0.58 g, $3.6 \times 10^{-3}$ mol). The resulting solution was stirred at ambient temperature for three hours, during which time a gas ($CO_2$) was evolved. A solution of 3-[1-(3-chlorophenyl)-4-piperazinyl]aminopropane (0.92 g, $3.6 \times 10^{-3}$ mol) in 25 mL of chloroform was then added, and the resulting reaction mixture was stirred under nitrogen at ambient temperature for 2 days. The mixture was diluted to 150 mL with chloroform, washed with three-one hundred mL portions of water, dried over anhydrous sodium sulfate, and concentrated on a rotary evaporator. The desired product (TLC on silica using a 20% methanol in ethyl acetate solvent system, $R_f = 0.52$) was isolated by gravity chromatography on silica gel and converted to the hydrochloride salt (0.74 g, 47% yield), m.p. 236°-237° C.

Anal. Calcd. $C_{23}H_{32}ClN_3O \cdot HCl$: C, 63.00; H, 7.59; N, 9.58%. Found: C, 62.84; H, 7.66; N, 9.57%.

EXAMPLE 20

The compounds of the invention were evaluated for their ability to inhibit limbic D-2 dopamine receptor binding. This in vitro assay measures the ability of the compounds tested to bind to the dopamine receptor sites. Those compounds which exhibit a high binding effect have a high potential to display antipsychotic effects.

The test is carried out as follows:

Several rats are decapitated and the brains are rapidly removed. Limbic brain tissue (nucleus accumbens, septal area, olfactory tubercle) is dissected and homogenized on ice in 9 volumes of buffer (50 mM Tris-HCl, 120 mM NaCl, 5 mM KCl, 1 mM $CaCl_2$, 1 mM $MgCl_2$, 0.1% L-ascorbic acid, 10 μM pargyline HCl, pH 7.1) using a Polytron homogenizer at setting 5 for three 15-second bursts. The homogenate is then diluted 4-fold with buffer and centrifuged at 30,000×g for 20 minutes, and the supernatant is discarded. The pellet is resuspended in the same volume of buffer and recentrifuged as before, again discarding the supernatant. This pellet is then resuspended in the same volume of buffer used in the homogenization, and the protein content of this preparation is assayed by the Lowry method. The homogenate is stored frozen at −70° C. until use.

Thirty μL of the homogenate (0.2–0.3 mg protein/sample) are incubated with 0.3 nM $^3$H-spiroperidol (New England Nuclear) and various concentrations of test drug in a final volume of 1 mL of the above buffer for 10 minutes in a 37° C. water bath. All tubes contained 30 nM ketanserin to exclude binding to 5-$HT_2$ receptors. At the end of the incubation, 3 mL of cold 50 mM Tris-HCl, pH 7.7, are added to each tube, and the contents are rapidly vacuum-filtered through Whatman GF/B glass-fiber filters. The filters are then rapidly washed 3 times with 3 mL of the same buffer, placed in scintillation vials, and shaken for 15 minutes with 10 mL of Hydrofluor (National Diagnostics) scintillation cocktail. The vials are then counted in a Packard 460 CD scintillation counter.

Specific binding is defined as total binding less binding in the presence of 10 μM sulpiride. Binding in the presence of various concentrations of test drug is expressed as a percent of specific binding when no drug is present. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H\text{-Spiroperidol}]}{K_D}}$$

where $K_D = 0.3$ nM for spiroperidol binding

| Standard Compounds: | $K_i$ and 95% confidence interval |
|---|---|
| Haloperidol | 4.0 (3.0–5.6) nM |
| Clozapine | 181 (113–362) nM |
| Fluphenazine | 4.5 (3.6–5.6) nM |
| Sulpiride | 634 (348–1385) nM |

The results of testing of some of the compounds of the invention, and the prior art compound gepirone (4,4-dimethyl-1-[4-[4-(2-pyrimidinyl)-1-piperazinyl]-butyl]-2,6-piperidinedione) in this assay are presented in Table 1.

The results show that compounds of the invention display affinity for the $D_2$ receptor, evidencing potential for antipsychotic effects.

EXAMPLE 21

The in vitro inhibition of 5-$HT_{1A}$ serotonin receptor binding is used to determine whether the test compounds possess affinity at 5-$HT_{1A}$ receptors and whether there is an indication of gepirone-like anxiolytic activity.

The assay is carried out as follows:

Hippocampal tissue from male Sprague Dawley rats is dissected and homogenized on ice in 40 volumes of buffer A (50 mM Tris HCl, pH=7.7) using a Polytron homogenizer at setting 5 for 3×15 second bursts. The homogenate is then centrifuged at 20,000 rpm (RC5-B; 50,000 g) and the supernatant discarded. The pellet is resuspended in 40 volumes of the same buffer and incubated at 37° C. for 10 minutes to aid in the removal of endogenous serotonin. The homogenate is then centrifuged (as above) and the supernatant discarded. The pellet is then resuspended in 100 volumes of buffer B (50 mM Tris HCl, pH=7.7 containing 0.1% ascorbate, 10 μM pargyline and 4 mM $CaCl_2$) and sonicated. An aliquot is taken for protein determination by the Lowry method and the remainder stored frozen at −70° C. until used.

The homogenate (50 μL; 0.4–0.6 mg protein/sample) is incubated with 100 μL (1.5–1.8 nM) $^3$H-8-hydroxy-2-(di-n-propylamino)tetraline ($^3$H-8-OH-DPAT) in a final volume of 2 mL of buffer for 10 minutes at 37° C. At the end of the incubation, 3 mL of cold buffer A are added to each tube, and the contents rapidly filtered through Whatman BF/B glass filters. The filters are then rapidly washed 2 times with 3 mL of the same buffer, placed in scintillation vials, and shaken for 15 minutes with 10 mL of Hydrofluor (National Diagnostics) scintillation cocktail. The vials are then counted in a Packard 460 CD scintillation counter.

Specific binding is defined as total binding less binding in the presence of excess unlabeled serotonin (1 μM). Binding in the presence of various concentrations of test drug is expressed as a percent of specific binding when no drug is present. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H\text{-8-OH-}DPAT]}{K_D}}$$

where $K_D = 1.8$ nM for 8-OH-DPAT binding in hippocampus

When tested in this assay, the compounds of the invention gave the results set forth in Table 1.

The results show that compounds of the invention have a moderate to very high affinity for the 5-$HT_{1A}$ receptor site, evidencing a high potential for anxiolytic activity.

EXAMPLE 22

5-$HT_2$ inhibition of $^3$H-spiroperidol is determined in an analogous manner, employing rat brain cortex homogenate as the receptor tissue, following a modification of Fields et al, Brain Res., 136, 578 (1977); Yamamura et al, eds., Neurotransmitter Receptor Binding, Raven Press, N.Y. 1978; and Creese et al, Eur. J. Pharmacol., 49, 20 (1978).

The assay is carried out as follows:

Several rats are decapitated and the brains are rapidly removed. Cortical tissue is dissected and homogenized on ice in 9 volumes of buffer (50 mM Tris-HCl, 120 mM NaCl, 5 mM KCl, 1 mM $CaCl_2$, 1 mM $MgCl_2$, 0.1% L-ascorbic acid, 10 μM pargyline HCl, pH 7.1) using a Polytron homogenizer at setting 5 for 3 15-second bursts. The homogenate is then diluted 4-fold with buffer and centrifuged at 30,000×g for 20 minutes and the supernatant is discarded. The pellet is resuspended in the same volume of buffer and recentrifuged as before, again discarding the supernatant. This pellet is then resuspended in the same volume of buffer used in the homogenization, and the protein content of this preparation is assayed by the Lowry method. The homogenate is stored frozen at −70° C. until use.

Thirty μL of the homogenate (0.2–0.3 mg protein/sample) are incubated with 0.8 nM $^3$H-spiroperidol (New England Nuclear) and various concentrations of test drug in a final volume of 1 mL of the above buffer for 10 minutes in a 37° C. water bath. All tubes contained 1 μM sulpiride to exclude binding to $D_2$ receptors. At the end of the incubation, 3 mL of cold 50 mM Tris-HCl, pH 7.7, are added to each tube, and the contents are rapidly vacuum-filtered through Whatman GF/B glass-fiber filters. The filters are then rapidly washed 3 times with 3 mL of the same buffer, placed in scintillation vials, and shaken for 15 minutes with 10 mL of Hydrofluor (National Diagnostics scintillation cocktail. The vials are then counted in a Packard 460CD scintillation counter.

Specific binding is defined as total binding less binding in the presence of 10 μM Ketanserin. Binding in the presence of various concentrations of test drug is expressed as a percent of specific binding when no drug is present. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H\text{-Spiroperidol}]}{K_D}}$$

where $K_D$ = 0.8 nM for spiroperidol binding in cortex

When tested in this assay, the compounds of this invention gave the results set forth in Table 1.

EXAMPLE 23

The M1 muscarinic receptor binding properties of the compounds of this invention were established as follows:

Rat hippocampus tissue is homogenized using a teflon-coated pestle in 20 volumes of 0.32M sucrose and centrifuged (747×g for 10 minutes at 4° C.). The supernatant liquid is decanted and recentrifuged (18,677×g for 20 minutes at 4° C.). The resulting pellet is resuspended in the original volume of 0.32M aqueous sucrose. The sample is then diluted (1:1 v/v) in 10 mM $Na_2HPO_4/KH_2PO_4$ buffer (pH=7.4). A 100 μL sample of the buffered tissue suspension is incubated at 25° C. for 60 minutes in the dark with 10 μL of test compound or vehicle for control and [$^3$H] pirenzepine (0.5 nM, 0.04 μCi) q.s. 1 milliliter with the buffer solution. Atropine sulfate (2 μM) is added to half the samples being processed. Binding is terminated by vacuum filtration onto Whatman GF/B filters which are washed three times with the buffer solution (3 ml/wash, 4° C.). The radioactivity of the filter-trapped material is determined by liquid scintillation spectroscopy and the $IC_{50}$ (50% inhibition of specific [$^3$H] PZ binding) is calculated for the test compound. Specific [$^3$H] PZ binding is defined as total binding minus binding in the presence of 2 μM atropine sulfate.

EXAMPLE 24

The M2 receptor binding properties of the compounds of this invention were determined in the manner described for M1 receptor determinations with the following exceptions. Homogenized rat cerebellum tissue, diluted (1:2 v/v) in the above mentioned phosphate buffer, was employed for its M2 receptor sites and [$^3$H] quinuclidinyl benzilate (0.23 nM, 0.01 μCi) was employed as the muscarinic receptor ligand. The concentration of atropine sulfate used in these experiments was 100 μM. The assay tubes were incubated at 37° C. for 60 minutes.

The muscarinic M2 receptor subtype serves to control presynaptic acetylcholine release. Activation of the M2 receptor inhibits acetylcholine release, thereby exerting a negative influence on learning and memory processes which are at least partially regulated by the central cholinergic system. The muscarinic M1 receptor subtype is localized on the postsynaptic nerve cell where activation provides direct enhancement of the central cholinergic function. Enhancement of the central cholinergic function by direct stimulation of the M1 muscarinic receptor subtype provides one method of treatment for the central cholinergic dysfunction attending senile dementia of the Alzheimer type (SDAT) as a primary manifestation. Therefore, compounds to be used in the treatment of Alzheimer's disease and similar diseases involving memory impairment and learning disabilities should exhibit selectivity for the M1 receptor over the M2 muscarinic nervous system. The compound produced in Example 15 epitomizes the desired selective property in this case.

In qualitatively evaluating the above data, high affinity values for 5-$HT_{1A}$ receptors correlate (by analogy with buspirone) with anxiolytic/antidepressant activity, while lower values reflect a lesser activity. High affinity values for $D_2$ receptor binding (greater than 80%) begin to show some antipsychotic activity.

Hence, the compounds of this invention are antidepressant/anxiolytic agents useful in the treatment of depression and in alleviating anxiety and in the case of the products of Examples 3, 4, 6, 7, 14 and 15 they have some meaningful antipsychotic activity which is useful in the treatment of psychoses such as paranoia and schizophrenia. Central cholinergic activity is evidenced by the product of Example 15, which establishes the compounds as useful in the treatment of SDAT, and the like diseases attending cholinergic hypofunction. As such, the compounds of this invention may be administered to a patient in need thereof, either neat or with a conventional pharmaceutical carrier. The pharmaceutical carrier may be solid or liquid as suitable for oral or parenteral administration.

TABLE 1

| Affinity for 5-$HT_{1A}$ and 5-$HT_2$ Receptor Sites | | |
|---|---|---|
| % Inhibition at 1 μM or ($K_i$, nM) | % Inhibition at 100 nM | Affinity for $D_2$ Receptor Sites |

TABLE 1-continued

| Compound | 5-HT$_{1A}$ | 5-HT$_2$ | 5-HT$_{1A}$ | D$_2$ |
|---|---|---|---|---|
| Example 1 | 98% (1 nM) | 92% | — | 40% |
| Example 2 | 97% (1 nM) | 91% | — | 40% |
| Example 3 | 97% | — | — | 93% |
| Example 4 | 100% | — | — | 91% |
| Example 5 | 83% | — | — | 62% |
| Example 6 | 94% | — | — | 87% |
| Example 7 | 91% | — | — | 95% |
| Example 8 | 94% | — | — | 32% |
| Example 9 | 93% | — | — | 27% |
| Example 10 | 82% | — | — | 6% |
| Example 11 | 91% | — | — | 40% |
| Example 12 | 98% | — | — | 70% |
| Example 13 | 97% | — | — | 67% |
| Example 14 | — | — | 100% | 100% |
| Example 15 | — | — | 99% | 94% |
| Example 16 | — | — | — | — |
| Example 17 | 88% (67 nM) | — | — | 27% |
| Example 18 | 99% | — | — | 72% |
| Example 19 | (20 nM) | — | 75% | 31% |
| Gepirone | (65 nM) | 20% | (852 nM) | — |
| Buspirone | 94% (10 nM) | 46% | (78 nM) | — |
| Affinity for Muscarinic Acetylcholine Receptor Sites ||||
| Compound | IC$_{50}$ for M$_1$ | IC$_{50}$ for M$_2$ | M$_2$/M$_1$ Ratio ||
| Example 15 | 0.24 μM | 11 μM | 46 ||

In qualitatively evaluating the above data, high affinity values for 5-HT$_{1A}$ receptors correlate (by analogy with gepirone) with anxiolytic-antidepressant activity, while lower values reflect a lesser activity. Affinity values for D$_2$ receptors indicate some antipsychotic activity.

Hence, the compounds of this invention are antidepressant, anxiolytic agents useful in the treatment of depression and in alleviating anxiety and in the case of the products of Examples 3, 4, 6 and 7, they have in addition to anxiolytic activity some meaningful antipsychotic activity which is useful in the treatment of psychoses such as paranoia and schizophrenia. As such, they may be administered to a patient in need thereof, either neat or with a conventional pharmaceutical carrier.

We claim:

1. A compound having the formula

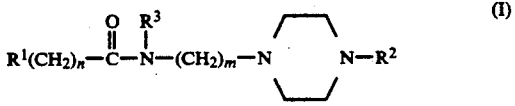

wherein R$^1$ is 1-adamantyl, 3-methyl-1-adamantyl, 3-noradamantyl, unsubstituted or substituted-2indolyl, 3-indolyl wherein the substituents are selected from lower alkyl, lower alkoxy and halo; R$^2$ is unsubstituted or substituted phenyl, benzyl or pyridinyl, wherein the substituents are selected from lower alkyl, lower alkoxy, trifluoromethyl and halo; R$^3$ is H or lower alkyl of 1 to 3 carbon atoms; n is the integer 0 or 1; and m is the integer from 2 to 5; or a pharmaceutically acceptable salt thereof.

2. A compound according to claim 1 wherein R$^1$ is 1-adamantyl, 3-methyl-1-adamantyl, 2-indolyl; R$^2$ is unsubstituted or substituted phenyl, wherein the substituents are selected from methoxy and chloro, pyridinyl; R$^3$ is H; n is the integer 0 or 1; m is the integer 2 or 3 or a pharmaceutically acceptable salt thereof.

3. A pharmaceutical composition comprising a compound of structure (I), or a pharmaceutically acceptable salt thereof, as defined in claim 1, and a pharmaceutically acceptable carrier.

* * * * *